(12) United States Patent
Sfeir et al.

(10) Patent No.: US 10,585,043 B2
(45) Date of Patent: Mar. 10, 2020

(54) ULTRATHIN FILM LASING

(71) Applicant: Brookhaven Science Associates, LLC, Upton, NY (US)

(72) Inventors: Matthew Y. Sfeir, Bethpage, NY (US); Kannatassen Appavoo, Birmingham, AL (US); Xiaoze Liu, Berkeley, CA (US); Vinod M. Menon, New York, NY (US)

(73) Assignees: Brookhaven Science Associates, LCC, Upton, NY (US); Research Foundation of The City University of New York, New York, NY (US)

( * ) Notice: Subject to any disclaimer, the term of this patent is extended or adjusted under 35 U.S.C. 154(b) by 200 days.

(21) Appl. No.: 15/586,821

(22) Filed: May 4, 2017

(65) Prior Publication Data
US 2017/0324215 A1     Nov. 9, 2017

Related U.S. Application Data

(60) Provisional application No. 62/331,735, filed on May 4, 2016.

(51) Int. Cl.
*G01N 21/64* (2006.01)
*H01S 5/34* (2006.01)
*H01S 3/16* (2006.01)

(52) U.S. Cl.
CPC ......... *G01N 21/6489* (2013.01); *H01S 3/169* (2013.01); *H01S 5/3412* (2013.01)

(58) Field of Classification Search
CPC .... G01N 21/6489; G01N 21/64; H01S 3/169; H01S 5/3412; H01S 5/0281; H01S 5/0206

USPC ..................................................... 250/458.1
See application file for complete search history.

(56) References Cited

U.S. PATENT DOCUMENTS

2008/0267227 A1* 10/2008 Seo ...................... H01S 3/06754
372/6
2017/0074640 A1* 3/2017 Cable ................. G01B 9/02083

FOREIGN PATENT DOCUMENTS

CN         103022898 A     4/2013

OTHER PUBLICATIONS

Wiersma, D. S. et al. "Light Diffusion with Gain and Random Lasers" Phys. Rev. E: Stat. Phys., Plasmas, Fluids, Relat. Interdiscip. Top. 54, 4256-4265 (1996). DOI:10.1103/PhysRevE.54.4256.

(Continued)

*Primary Examiner* — David P Porta
*Assistant Examiner* — Meenakshi S Sahu
(74) *Attorney, Agent, or Firm* — Dorene M. Price

(57) ABSTRACT

Technologies are described for methods to fabricate lasers to amplify light. The methods may comprise depositing nanoparticles on a substrate. The length, width, and height of the nanoparticles may be less than 100 nm. The methods may further comprise distributing the nanoparticles on the substrate to produce a film. The nanoparticles in the film may be coupled nanoparticles. The coupled nanoparticles may be in disordered contact with each other within the film. The distribution may be performed such that constructive interference of the light occurs by multiple scattering at the boundaries of the coupled nanoparticles within the film. The methods may comprise exposing the film to a power source.

20 Claims, 7 Drawing Sheets

(56) References Cited

OTHER PUBLICATIONS

Berger, G. A. et al. "Dynamics of Stimulated Emission from Random Media" Phys. Rev. E: Stat. Phys. Plasmas, Fluids, Relat. Interdiscip. Top. 56, 6118-6122 (1997). DOI:10.1103/PhysRevE.56.6118.

Cao, H. et al. "Random Laser Action in Semiconductor Powder" Phys. Rev. Lett. 82, 2278-2281 (1999). DOI:10.1103/PhysRevLett.822278.

Yamamoto, A et al. "Dynamics of Photoexcited Carriers in Zno Epitaxial Thin Films" Appl. Phys. Lett. 75, 469-471 (1999). DOI:10.1063/1.124411.

Apalkov, V. M. et al. Random Resonators and Prelocalized Modes in Disordered Dielectric Films. Phys. Rev. Lett. 89, 016802 (2002). DOI:10.1103/PhysRevLett.89.016802.

Leskela, M. et al. "Atomic layer deposition (ALD): from precursors to thin film structures" Thin Solid Films 409 138146 (2002). DOI:10.1016/S0040-6090(02)00117-7.

Bauer, C. et al. "Ultrafast Relaxation Dynamics of Charge Carriers Relaxation in Zno Nanocrystalline Thin Films" Chem. Phys. Lett. 387, 176-181 (2004). DOI:10.1016/j.cplett.2004.01.106.

Toshine, Y. et al. "Conversion of an Electron-Hole Plasma into a High Density Excitonic State in Zno Epitaxial Thin Films" Phys. Status Solidi C 1, 839-842 (2004). DOI:10.1002/pssc.200304249.

Scholes G. D. et al. "Excitons in nanoscale systems," Nat. Mat. 5, 683 696 (2006). DOI:10.1038/nmat1710.

Hendry, E. et al. "Exciton and Electron-Hole Plasma Formation Dynamics in Zno" Phys. Rev. B: Condens. Matter Mater. Phys. 76, 045214 (2007). DOI:10.1103/PhysRevB.76.045214.

Klimov, V. I. et al. "Single-Exciton Optical Gain in Semiconductor Nanocrystals" Nature 447, 441-446 (2007). DOI:10.1038/nature05839.

Ma, X. et al. "Electrically pumped ZnO film ultraviolet random lasers on silicon substrate" Applied Physics Letters 91, 251109 (2007). DOI:10.1063/1.2826543.

Zhang, X. H. et al. "Exciton Radiative Lifetime in Zno Nanorods Fabricated by Vapor Phase Transport Method" Appl. Phys. Lett. 90, 013107 (2007). DOI:10.1063/1.2429019.

Cooney, R. R. et al. "Gain Control in Semiconductor Quantum Dots via State-Resolved Optical Pumping" Phys. Rev. Lett. 102, 127404 (2009). DOI:10.1103/PhysRevLett.102.127404.

Cooney, R. R. et al. "State-Resolved Manipulations of Optical Gain in Semiconductor Quantum Dots: Size Universality Gain Tailoring, and Surface Effects" J. Chem. Phys. 131, 164706 (2009). DOI:10.1063/1.3254199.

Fallert, J. Et al. "Co-Existence of Strongly and Weakly Localized Random Laser Modes" Nat. Photonics 3, 279-282 (2009). DOI:10.1038/nphoton.2009.67.

Fujiwara, H. et al. "Numerical Analysis of Resonant and Lasing Properties at a Defect Region within a Random Structure" Opt. Express 17, 3970-3977 (2009). DOI:10.1364/OE.17.003970.

Sewall, S. L "Direct Observation of the Structure of Band-Edge Biexcitons in Colloidal Semiconductor Cdse Quantum Dots" Phys. Rev. B: Condens. Matter Mater. Phys. 80, 081310 (2009). DOI:10.1103/PhysRevB.80.081310.

Ivanov, S. A. et al. "Spectral and Dynamic Properties of Excitons and Biexcitons in Type-Ii Semiconductor Nanocrystals" ACS Nano, 4, 5994-6000 (2010). DOI: 10.1021/nn101357q.

Klingshirn, C. et al. "65 Years of Zno Research—Old and Very Recent Results" Phys. Status Solidi B, 247, 1424-1447 (2010). DOI:10.1002/pssb.201090010.

Zhu, H. et al. "Low-Threshold Electrically Pumped Random Lasers" Adv. Mater22, 18771881 (2010). DOI:10.1002/adma.200903623.

Zimmler, M. A. et al. "Optically Pumped Nanowire Lasers: Invited Review" Semicond. Sci. Technol. 25, 024001 (2010). DOI:101088/0268-1242/25/2/024001.

Guillet, T. et al. "Laser Emission with Excitonic Gain in a Zno Planar Microcavity" Appl. Phys. Lett. 98, 211105 (2011). DOI:10.1063/1.3593032.

Li, Y. et al. "Remarkable decrease in threshold for electrically pumped random ultraviolet lasing from ZnO film by incorporation of Zn2TiO4 nanoparticles" Opt. Express 19, 8662-8669 (2011). DOI:10.1364/OE.19.008662.

Ma, R.-M. et al. "Room-Temperature Sub-Diffraction-Limited Plasmon Laser by Total Internal Reflection" Nat. Mater. 10, 110-113 (2011). DOI:10.1038/nmat2919.

Versteegh, M. A. M. et al. "Ultrafast Screening and Carrier Dynamics in Zno: Theory and Experiment" Phys. Rev. B: Condens. Matter Mater. Phys. 84, 035207 (2011). DOI:10.1103/PhysRevB.84.035207.

Wang, J. et al. "Transport through Modes in Random Media" Nature, 471, 345-348 (2011). DOI:10.1038/nature09824.

Xing, G. et al. "Charge Transfer Dynamics in Cu-Doped Zno Nanowires" Appl. Phys. Lett. 98, 102105-3 (2011). DOI:10.1063/1.3558912.

Dang, C. et al "Red, Green and Blue Lasing Enabled by Single-Exciton Gain in Colloidal Quantum Dot Films" Nat. Nanotechnol. 7, 335-339 (2012). DOI:101038/nnano.2012.61.

Kong, K. et al. "Low-threshold ZnO random lasing in a homojunction diode with embedded double heterostructure" Appl Phys A (2012) 107:971975. DOI:10.1007/s00339-012-6850-5.

Moreels, I. et al. "Nearly Temperature-Independent Threshold for Amplified Spontaneous Emission in Colloidal Cdse/Cds Quantum Dot-in-Rods" Adv. Mater. 24, OP231-OP235 (2012). DOI:10.1002/adma.201202067.

Nakamura, T. et al. Electron-Hole Plasma Lasing in a Zno Random Laser. Phys. Rev. B: Condens. Matter Mater. Phys. 86, 205103 (2012). DOI:10.1103/PhysRevB.86.205103.

Busby, E. et al. "Ultrafast Exciton Dynamics in Colloidal Aluminum Phosphide Nanocrystals" Chem. Phys. Lett. 557, 129-133 (2013). DOI:10.1016/j.cplett.2012.12.032.

Liu, X. et al. "Formation of microcavity polaritons in ZnO nanoparticles," Opt. Express 21, 532536 (2013). DOI:10.1364/OE.21.020620.

Mehl, B. P. et al. Pump-Probe Microscopy: Spatially Resolved Carrier Dynamics in Zno Rods and the Influence of Optical Cavity Resonator Modes. J. Phys. Chem. B 117, 4390-4398 (2013). DOI:10.1021/jp307089h.

Almand-Hunter, A. E. et al. "Quantum Droplets of Electrons and Holes" Nature 506, 471-475 (2014). DOI: 10.1038/nature12994.

Appavoo, K. et al. "Role of size and defects in ultrafast broadband emission dynamics of ZnO nanostructu res". Applied Physics Letters 104, 133101 (2014). DOI:10.1063/1.4868534.

Appavoo, K. et al. "Enhanced broadband ultrafast detection of ultraviolet emission using optical Kerr gating." Review of Scientific Instruments 85 (5), 055114 (2014). DOI:10.1063/1.4873475.

Cirloganu, C. M. et al. "Enhanced Carrier Multiplication in Engineered Quasi-Type-II Quantum Dots" Nat. Commun. 5, 4148 (2014). DOI:10.1038/ncomms5148.

Feng, L. et al. "Single-Mode Laser by Parity-Time Symmetry Breaking" Science, 346, 972-975 (2014). DOI:10.1126/science.1258479.

Guzelturk, B.et al. "Amplified Spontaneous Emission and Lasing in Colloidal Nanoplatelets" ACS Nano 8, 6599-6605 (2014). DOI:10.1021/nn5022296.

Nakamura, T. et al. "Origins of Lasing Emission in a Resonance-Controlled Zno Random Laser" New J. Phys. 16, 093054 (2014). DOI:10.1088/1367-2630/16/9/093054.

Appavoo, K. et al. "Quantifying Bulk and Surface Recombination Processes in Nanostructured Water Splitting Photocatalysts via in Situ Ultrafast Spectroscopy" Nano Lett. 15, 1076-1082 (2015). DOI:10.1021/nl504035j.

Appavoo, K. et al. "Room-Temperature Exciton Lasing in Ultrathin Film of Coupled Nanocrystals" CLEO: 2015 Postdeadline Paper Digest Optical Society of America paper JTh5B.1 (2015). DOI:10.1364/CLEO_AT.2015.JTh5B.1.

* cited by examiner

US 10,585,043 B2

ULTRATHIN FILM LASING

CROSS REFERENCE TO RELATED APPLICATION

This application claims priority to Provisional Application No. 62/331,735 filed May 4, 2016, titled "Ultrathin Film Lasing", the entirety of which is hereby incorporated by reference.

STATEMENT OF GOVERNMENT RIGHTS

The present invention was made with government support under contract numbers DE-AC02-98CH10886 and DE-SC0012704, awarded by the U.S. Department of Energy, and DMR1105392, awarded by the National Science Foundation. The United States government has certain rights in this invention.

FIELD OF THE INVENTION

This disclosure relates generally to lasing in ultrathin films.

BACKGROUND

In a laser, a gain medium is a material with properties that allow it to amplify light by way of stimulated emission. Stimulated emission is a process when an electron in an atom makes a transition from a higher to a lower energy state and produces an additional photon.

SUMMARY

In some examples, methods for fabricating a laser to amplify light are generally described. The methods may comprise depositing nanoparticles on a substrate. The length, width, and height of the nanoparticles may be less than 100 nm. The methods may comprise distributing the nanoparticles on the substrate to produce a film. The nanoparticles in the film may be coupled nanoparticles. The coupled nanoparticles may be in disordered contact with each other within the film. The distribution may be performed such that constructive interference of the light occurs by multiple scattering at the boundaries of the coupled nanoparticles within the film. The methods may comprise exposing the film to a power source.

In some examples, lasers are described. The lasers may comprise a power source effective to produce light. The lasers may comprise a substrate in optical communication with the power source. The substrate may include a film. The film may include nanoparticles. The length, width, and height of the nanoparticles may be below 100 nm. The nanoparticles in the film may be coupled nanoparticles. The coupled nanoparticles may be in disordered contact with each other within the film. A distribution of the coupled nanoparticles on the substrate may be effective to produce constructive interference of the light by multiple scattering at the boundaries of coupled nanoparticles within the film.

In some examples, sensing devices are generally described. The sensing devices may comprise a substrate. The sensing devices may comprise a film on the substrate. The film may include nanoparticles. The length, width, and height of the nanoparticles may be below 100 nm. The nanoparticles in the film may be coupled nanoparticles. The coupled nanoparticles may be in disordered contact with each other within the film. A distribution of the coupled nanoparticles on the substrate may be effective to produce constructive interference of a first light by multiple scattering at boundaries of coupled nanoparticles within the film. The sensing devices may comprise a sensing element. The sensing element may be in optical communication with the film. The film may be effective to receive the first light and emit second light. A quantity of lumens of the second light may be greater than a quantity of lumens of the first light. The sensing element may be effective to detect the second light and generate a response.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

Figure 1:
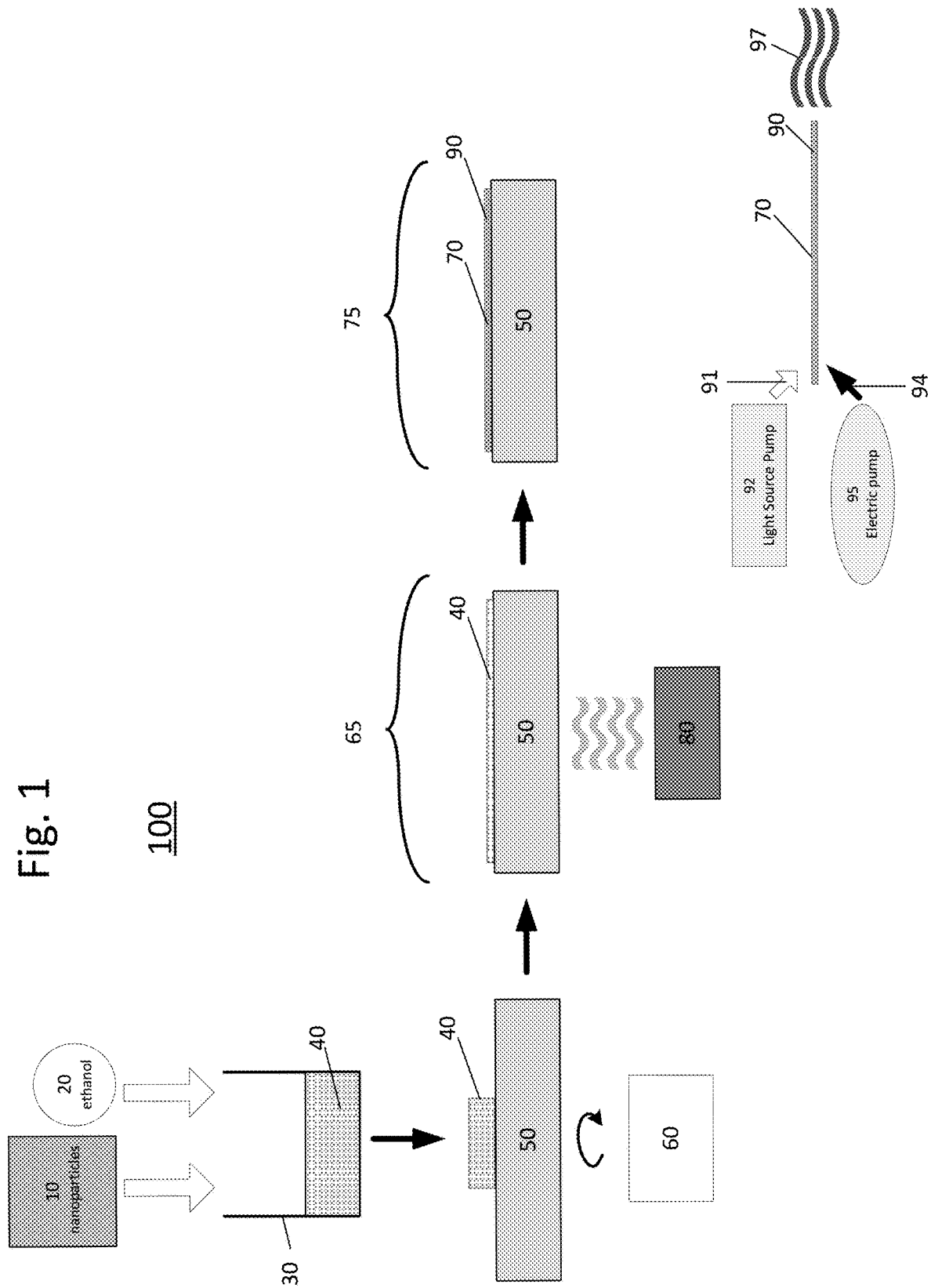
FIG. 1 is a system drawing illustrating a system to make and use an ultrathin film for ultrathin film lasing.

all arranged according to at least some embodiments described herein.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

As used herein, any compound, material or substance which is expressly or implicitly disclosed in the specification and/or recited in a claim as belonging to a group or structurally, compositionally and/or functionally related compounds, materials or substances, includes individual representatives of the group and all combinations thereof.

FIG. 1 is a system drawing illustrating a system 100 to make and use an ultrathin film for ultrathin film lasing, arranged in accordance with at least some embodiments presented herein. Nanoparticles 10 may be placed in a chamber 30. The nanoparticles 10 may be nanoparticles of any shape including a rounded object such as a tube, rod, ellipsoid, ovoid, or sphere, with all three dimensions of length, width, and height below 100 nm. A cross section of the nanoparticles 10 may similarly be under 100 nm. Nanoparticles 10 may include, for example, zinc oxide, gallium arsenide, and nitrides or oxides of Group II-VI or Group III-V semiconductors. In an example, the nanoparticles 10 may be nanospheres of zinc oxide (ZnO) with radii of 35-50 nm. An organic solvent 20 may be placed into chamber 30. Organic solvent 20 may be polar, non-polar, protic, or non-protic. Organic solvent 20 may include ethanol. Nanoparticles 10 may disperse within organic solvent 20 to form solution 40. Solution 40 may be deposited on a center of a substrate 50. Substrate 50 may have any thickness or conductivity, may be flexible, and may be transparent. Substrate 50 may include glass, silicon, ITO covered glass, or metal thin-films. For example substrate 50 may be borosilicate glass, soda lime glass, quartz, PYREX, or other suitable glass material. In some implementations, substrate 50 may have a thickness of 0.3, 0.5 or 0.7 millimeters, although in some implementations substrate 50 may be thicker (such as tens of millimeters) or thinner (such as less than 0.3 millimeters). In some implementations, substrate 50 may be non-glass, such as polycarbonate, acrylic, polyethylene terephthalate (PET) or polyether ether ketone (PEEK). In some implementations, substrate 50 may be non-transparent, such as a metal foil or stainless steel-based.

Substrate 50 may be rotated by spin coater 60. Spin coater 60 may spin substrate 50 at 8,000 to 12,000 rpm. Solution 40 may be distributed over surface of substrate 50 by centrifugal force during spin coating. Spin coated solution 40 and substrate 50 may form a sample 65.

Sample 65 may be heated by heater 80. Heater 80 may heat sample 65 to a temperature between about 250° C. to about 350° C. Organic solvent 20 in solution 40 may evaporate out of solution 40 when heated. Heating sample 65 may produce sample 75. Sample 75 may include substrate 50 coated with film 70. Film 70 may have a thickness of between 100 nm to 200 nm. Film 70 may include 3-4 layers of nanoparticles 10. A thickness of film 70 may be less than a wavelength ($\lambda$) of light emitted from film 70 upon lasing. A thickness of film 70 may be $\sim \lambda_{emission}/4$. Film 70 may include coupled nanoparticles 90 distributed on the substrate. Coupled nanoparticles 90 may be nanoparticles 10 in film 70 which may be in random, disordered, and non-uniform contact with each other within film 70. Coupled nanoparticles 90 may include nanoparticles that have surface areas in contact with surface areas of other nanoparticles. Coupled nanoparticles 90 may alternatively, or additionally, include nanoparticles that are not directly in contact but are electromagnetically connected with each other. Coupled nanoparticles 90 may produce a multiple scattering effect within film 70. Coupled nanoparticles 90 may be distributed on the substrate such that random, disordered, and non-uniform contact with each other within film 70 is effective to produce constructive interference of a light by multiple scattering of the light at the boundaries of coupled nanoparticles 90 within film 70. Multiple scattering produced by film 70 of coupled nanoparticles 90 may provide coherent interference of the light within film 70 and may be able to build an emission gain by trapping the light.

Other processes such as nanoimprint lithography, dip coating, inkjet printing, printing from solution, and matrix-assisted pulse laser evaporation of nanoparticles 10 may be used to produce film 70. Lasing may be induced in film 70 when film 70 is exposed to a power source such as a light source pump 92 or an electric pump 95. For example, film 70 may be effective to receive light 91 from light source pump 92 and emit spectra of light 97. A quantity of lumens of emitted spectra of light 97 may be greater than a quantity of lumens of light 91. In another example, film 70 may be effective to receive electricity 94 from electric pump 95 and emit spectra of light 97. Film 70 may be an ultrathin film of coupled nanoparticles 90 which when exposed to a power source such as a light source pump 92 or an electric pump 95 may emit light 97 and display room-temperature lasing. In an example, light source pump 92 may be effective to produce a 280 nm ultrafast pump pulse at about 100 fs to create a density of electron hole pairs above the optical bandgap in coupled nanoparticles 90 in film 70.

In an example, an ultrathin film was fabricated. A dilute solution of zinc oxide nanoparticles, with an average diameter of 35 nm were dispersed in ethanol. The solution was deposited on a glass substrate and spin-coated at 10,000 rpm. The spin-coated sample was then heated on a heating plate to 300° C. to remove the organic solvent. The resulting film was about 120 nm thick. Additional films were fabricated by the same process with varying thicknesses from 80 nm to 160 nm. Some of the additional films were annealed for a duration of about 5 minutes at 800° C. The various films fabricated were then evaluated with an ultrafast broadband optical Kerr spectrometer to produce time-resolved emission studies.

Figure 2:
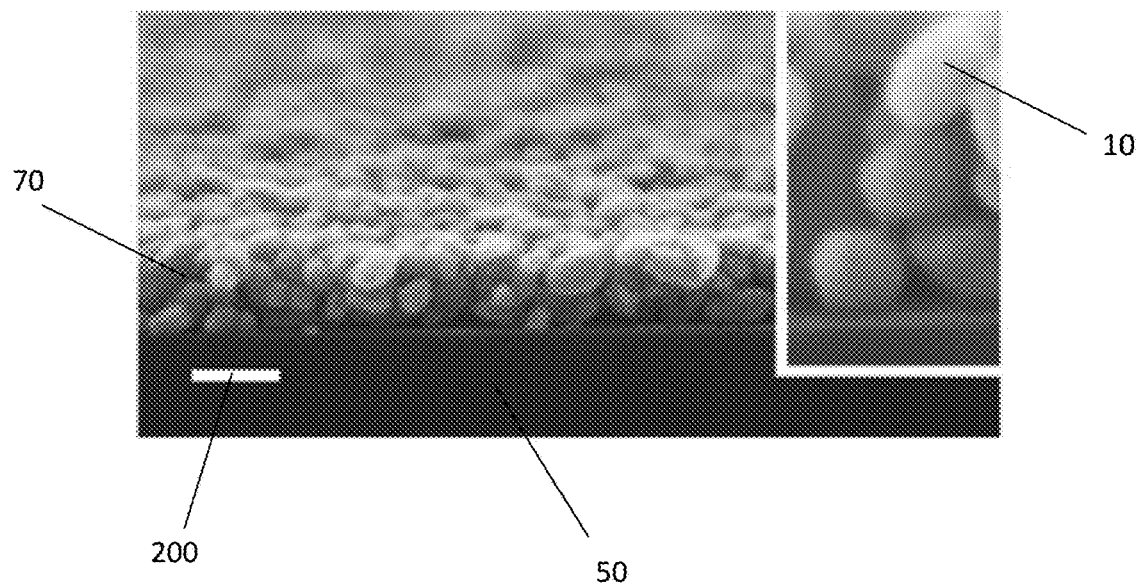
FIG. 2 is a drawing representing a scanning electron image of a film of ZnO coupled nanoparticles for ultrathin film lasing.

FIG. 2 is a scanning electron micrograph of a film of ZnO coupled nanoparticles for ultrathin film lasing arranged in accordance with at least some embodiments presented herein. Those components in FIG. 2 that are labeled identically to components of FIG. 1 will not be described again for the purposes of clarity. Film 70 may include nanoparticles 10. As shown in FIG. 2, film 70 may include 3-4 layers of nanoparticles 10. Scale bar 200 may be 100 nm in length. As indicated by scale bar 200, a thickness of film 70 may be about 100 nm and nanoparticles 10 may be nanoparticles with dimensions of about 35-50 nm in any direction.

Figure 3:
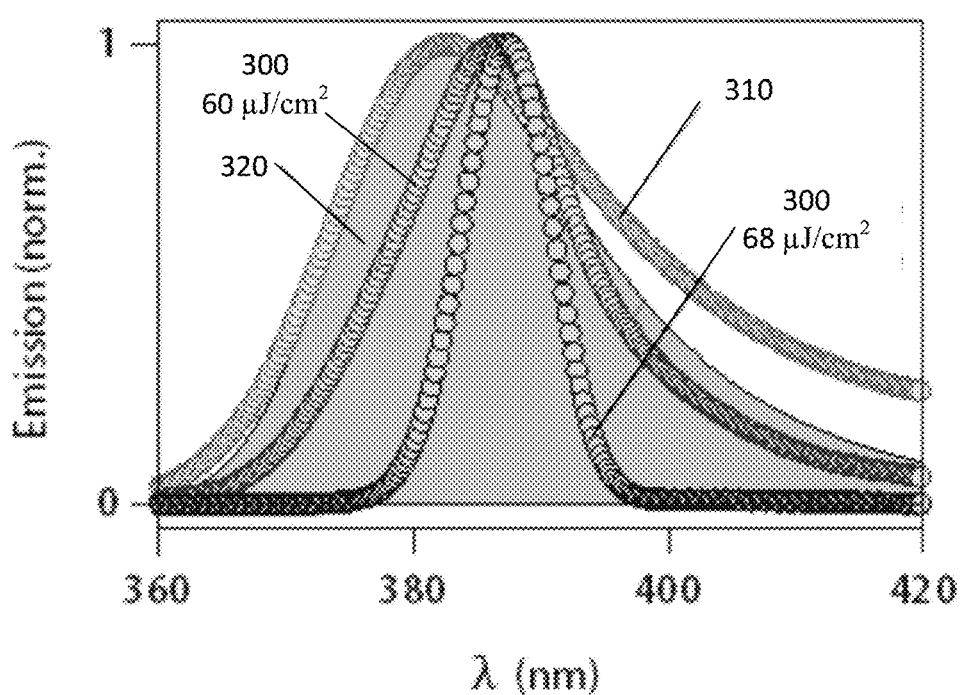
FIG. 3 is a graph of normalized emission spectra for a film of ZnO coupled nanospheres, a film of ZnO coupled nanospheres which was annealed, and ZnO nanospheres dispersed in ethanol.

FIG. 3 is a graph of normalized emission spectra for a film of ZnO coupled nanospheres 300, an annealed film of ZnO coupled nanospheres 310, and ZnO nanospheres dispersed in ethanol 320, arranged in accordance with at least some embodiments presented herein. An emission spectra may be the spectrum of frequencies of electromagnetic radiation emitted when an atom makes a transition from a high energy state to a low energy state. The collection of transitions may lead to different wavelengths and may comprise the emission spectra. Normalized emission spectra for a film of ZnO coupled nanospheres 300 may be shown for spectra near fluence thresholds of 60 µJ/cm$^2$ and 68 µJ/cm$^2$. Annealed film of ZnO coupled nanospheres 310 may display a broader linewidth due to emission from interfacial defect states which may contribute to a lower energy tail of the band-edge emission.

Figure 4:
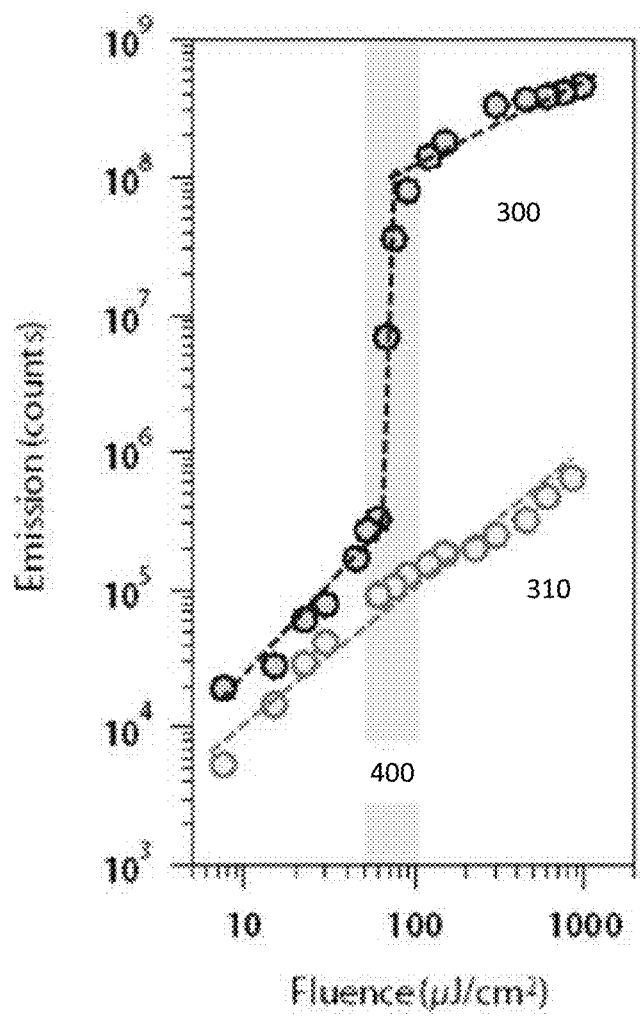
FIG. 4 is a graph of emission intensity as a function of pump fluence for the film of ZnO coupled nanospheres and the annealed film of ZnO coupled nanospheres.

FIG. 4 is a graph of emission intensity as a function of pump fluence for the film of ZnO coupled nanospheres 300 and annealed film of ZnO coupled nanospheres 310, arranged in accordance with at least some embodiments presented herein. FIG. 4 illustrates emission counts increase exponentially for ZnO coupled nanospheres 300 at a fluence threshold range 400 while emission counts increase only linearly as fluence increases for annealed film of ZnO coupled nanospheres 310. Fluence threshold range 400 may be 60 µJ/cm$^2$ to 68 µJ/cm$^2$. At fluence threshold range 400 emission counts of the film of ZnO coupled nanospheres 300 increased by 3 orders of magnitude from 10$^5$ to 10$^8$.

Figure 5A:
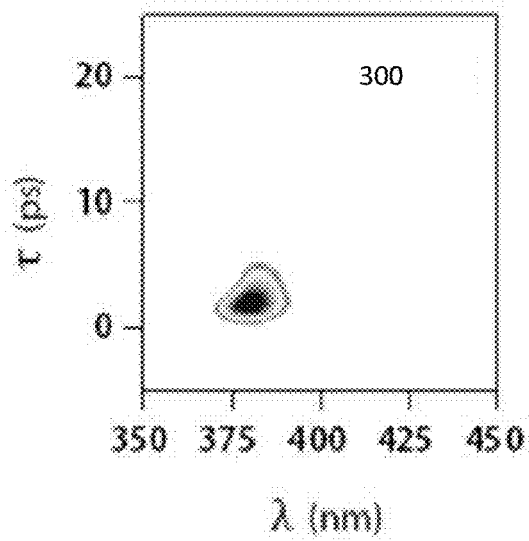
FIG. 5a is a graph of a two dimensional time-resolved emission measurement of the film of ZnO coupled nanospheres.
Figure 5B:
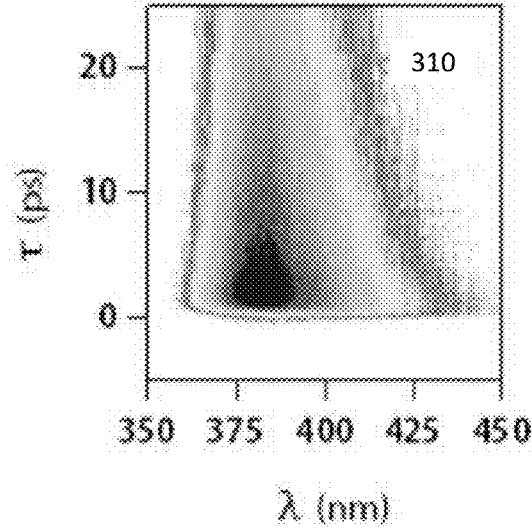
FIG. 5b is a graph of a two dimensional time-resolved emission measurement of the annealed film of ZnO coupled nanospheres.

FIG. 5a is a graph of a two dimensional time-resolved emission measurement of film of ZnO coupled nanospheres 300, arranged in accordance with at least some embodiments presented herein. FIG. 5b is a graph of a two dimensional time-resolved emission measurement of annealed film of ZnO coupled nanospheres 310, arranged in accordance with at least some embodiments presented herein. FIG. 5a shows high intensity and short duration of the emitted light from film of ZnO coupled nanospheres 300, illustrating lasing in film of ZnO coupled nanospheres 300. The lasing is characterized by an ultrafast, picosecond time scale emission process that is at least an order of magnitude faster than films under non-lasing conditions. FIG. 5b illustrates no lasing and emission of light spread over time in annealed film of ZnO coupled nanospheres 310. The random lasing displayed in FIG. 5a is counterintuitive to commonly cited criteria of strongly scattering particles and an optically thick sample, in which the mean free path for scattering exceeds the thickness of the material. Predictions of the optimal size of a particle of ZnO to optimize resonant scattering at the band-edge emission wavelength is ~260 nm. FIGS. 5a and 5b illustrate lasing occurring in film of ZnO coupled nanospheres 300 of randomly scattered nanoparticles and lasing did not occur in annealed film of ZnO coupled nanospheres 310 where the nanoparticles are ordered and aligned through annealing.

Figure 6A:
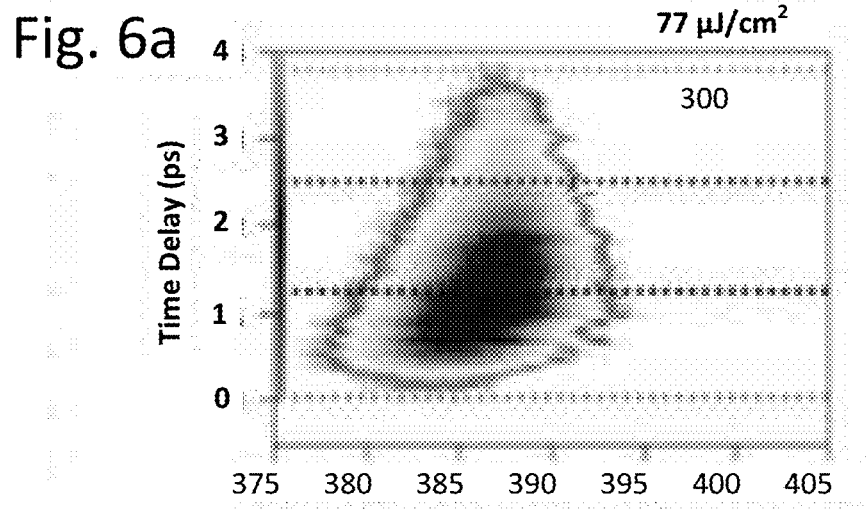
FIG. 6a is a graph of a slice of a two dimensional time-resolved emission measurement of film of ZnO coupled nanospheres 300.
Figure 6B:
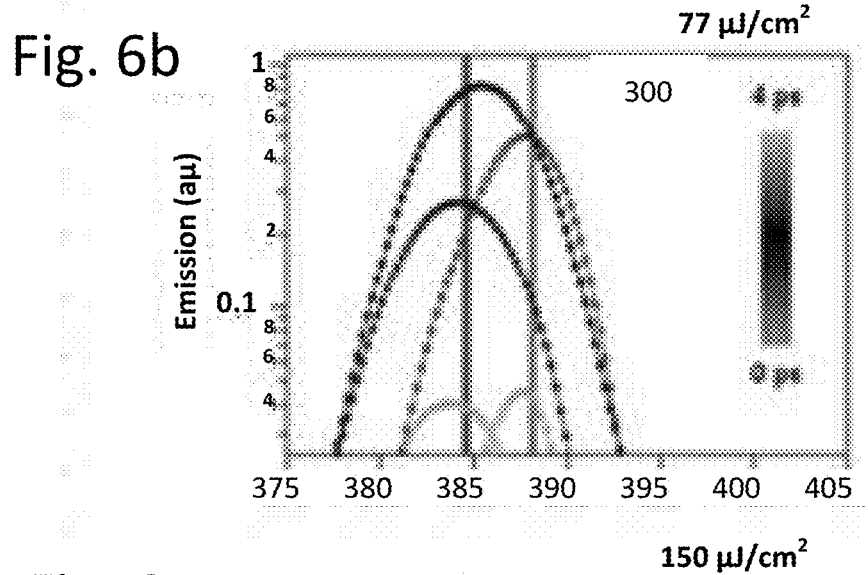
FIG. 6b is a graph of a slice of emission spectra at 0-4 ps for individual lasing modes of the film of ZnO coupled nanospheres at a fluence of 77 $\mu J/cm^2$.
Figure 6C:
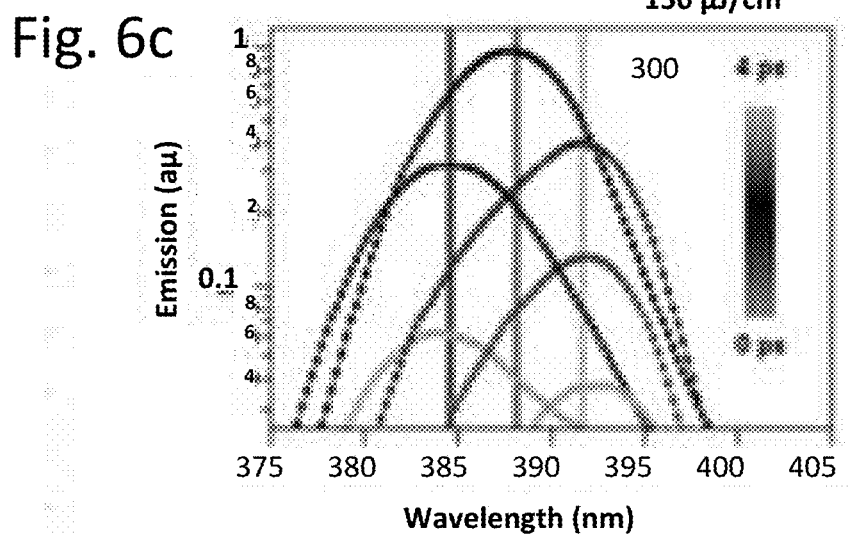
FIG. 6c is a graph of emission spectra at 0-4 ps for individual lasing modes of the film of ZnO coupled nanospheres at a fluence of 150 $\mu J/cm^2$.

FIG. 6a is a graph of a two dimensional time-resolved emission measurement of a film of ZnO coupled nanospheres 300, arranged in accordance with at least some embodiments presented herein. FIG. 6b is a graph of a slice of emission spectra at 0-4 ps for individual lasing modes of film of ZnO coupled nanospheres 300 at a fluence of 77 µJ/cm$^2$, arranged in accordance with at least some embodiments presented herein. FIG. 6c is a graph of a slice of emission spectra at 0-4 ps for individual lasing modes of film of ZnO coupled nanospheres 300 at a fluence of 150 µJ/cm2, arranged in accordance with at least some embodiments presented herein. FIG. 6a shows the lasing modes of film of ZnO coupled nanospheres 300 at 77 µJ/cm$^2$ as a function of time in picoseconds and wavelength of the emission. FIG. 6b shows distinct temporal characteristics of individual lasing modes of film of ZnO coupled nanospheres 300 at a fluence of 77 µJ/cm$^2$. FIG. 6c shows distinct temporal characteristics of individual lasing modes of film of ZnO coupled nanospheres 300 at a fluence of 150 µJ/cm2. The showing of discrete lasing modes in the absence of an external optical cavity indicates random lasing in film of ZnO coupled nanospheres 300. Sub-diffraction length scales of film of ZnO coupled nanospheres 300 may confine the incoming light fields within film of ZnO coupled nanospheres 300 and selectively outcompete extended modes that allow the emitted photons to diffuse throughout film of ZnO coupled nanospheres 300. The size of nanospheres in film of ZnO coupled nanospheres 300 may allow for a close-packing arrangement with minimum void sizes in the form of air pockets. For example, decreasing the nanosphere diameter from 200 nm to 35 nm may result in a decrease in void size by more than 90 percent and may allow more emitted photons to interact within film of ZnO coupled nanospheres 300. More emitted photons interacting within film of ZnO coupled nanospheres 300 may increase a coherent scattering process for light to be amplified, and may accelerate excitation delay via amplified stimulated emission.

Figure 7:
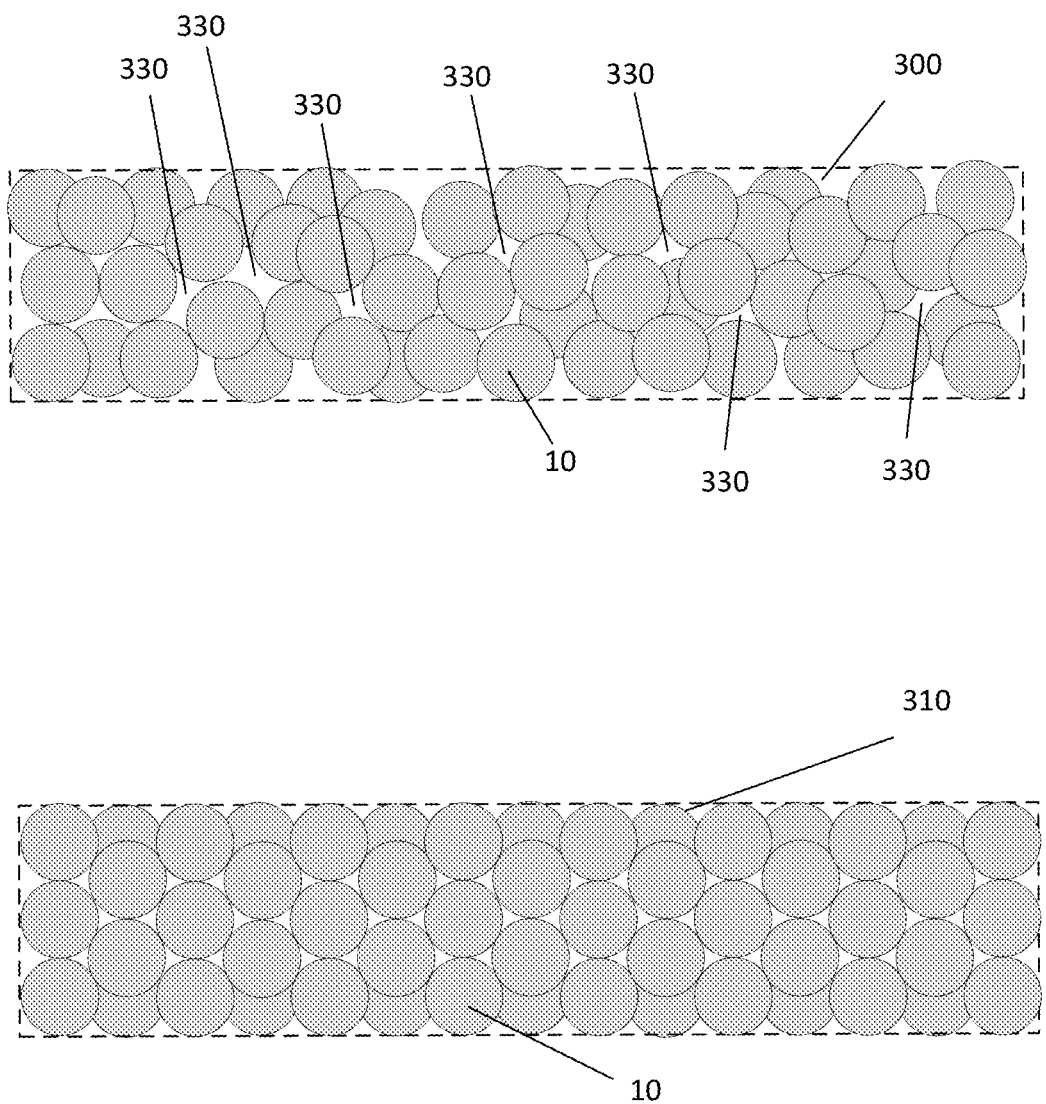
FIG. 7 is an illustration of the film of ZnO coupled nanospheres and the annealed film of ZnO coupled nanospheres.

FIG. 7 is an illustration of film of ZnO coupled nanospheres 300 and annealed film of ZnO coupled nanospheres 310, arranged in accordance with at least some embodiments presented herein. As shown in FIG. 7, film of ZnO coupled nanospheres 300 may include randomly scattered nanoparticles 10 and the randomly scattered nanoparticles may provide a geometry (density, size, film morphology) which is conducive to lasing. Randomly scattered nanoparticles 10 may form random sized and shaped boundaries 330 between the nanoparticles 10 within film of ZnO coupled nanospheres 300. Random boundaries 330 formed by coupled nanoparticles 10 and coupled nanoparticles 10 may provide coherent interference within the film and may be able to build an emission gain by trapping light. In annealed film of ZnO coupled nanospheres 310, nanoparticles 10 are aligned by fusing of nanoparticles 10 during annealing. Fusing of nanoparticles 10 during annealing may prevent lasing by causing changes in the scattering profile of annealed film of ZnO coupled nanospheres 310 and introducing interfacial trap states.

Figure 8:
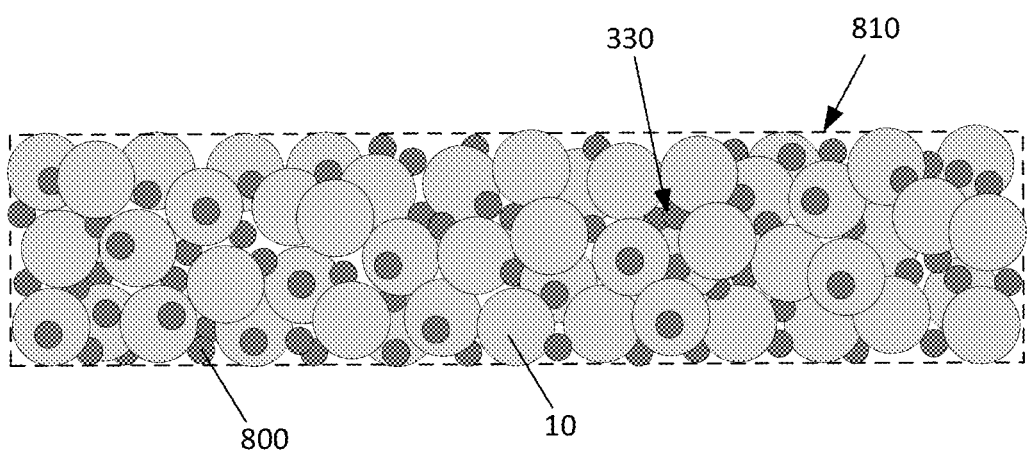
FIG. 8 is an illustration of film of ZnO coupled nanoparticles interspersed with a material.

FIG. 8 is an illustration of a film of ZnO coupled nanoparticles 10 and a material 800 interspersed among ZnO coupled nanoparticles 10, arranged in accordance with at least some embodiments presented herein. Those components in FIG. 8 that are labeled identically to components of FIGS. 1-7 will not be described again for the purposes of clarity. In an example, an ultrathin film 810 including ZnO coupled nanoparticles was made as described above in reference to FIGS. 1 and 7, and material 800 interspersed among ZnO coupled nanoparticles 10 was fabricated by atomic layer disposition (ALD). An exemplary ALD cycle may include flowing a material precursor into a reaction chamber that contains the ultrathin film 810 including ZnO coupled nanoparticles 10. The chamber may then be evacuated and a molecule reactive to the precursor may be introduced to the chamber. The ALD cycle may be repeated to fill boundaries 330 between coupled ZnO nanoparticles 10 to intersperse material 800 among coupled ZnO nanoparticles 10. In an embodiment, the material 800 forms a coating or film on the coupled ZnO nanoparticles 10.

The precursor may be any suitable precursor known in the art. In certain embodiments, the precursor is a halide, alkoxide, or an alkyl of a metal or metalloid, such as aluminum, titanium, hafnium, or silicon. In certain embodiments, the precursor may contain aluminum, such as for example aluminum trichloride, dimethylaluminum propoxide, tri-i-butylaluminum, triethylaluminum, triethyl(tri-sec-butoxy)dialuminum, trimethylaluminum, aluminum s-butoxide, aluminum ethoxide, aluminum i-propoxide, or dimethylaluminum i-propoxide. The molecule reactive to the precursor may be an oxidizing agent, such as for example oxygen, water, hydrogen peroxide, or ozone.

A refractive index of material 800 may be different from a refractive index of coupled nanoparticles 10 and material 800 may contribute to multiple scattering within film 810. Material 800 may have a higher bandgap than ZnO. Material 800 may be a dielectric. When material 800 is a dielectric, material 800 may prevent a short circuit between a first and second conductor placed on either side of film 810. Material 800 may include aluminum oxide, silicon oxide, titanium oxide, hafnium oxide, or any other dielectric material. Material 800 may increase multiple scattering within film 810.

Figure 9:
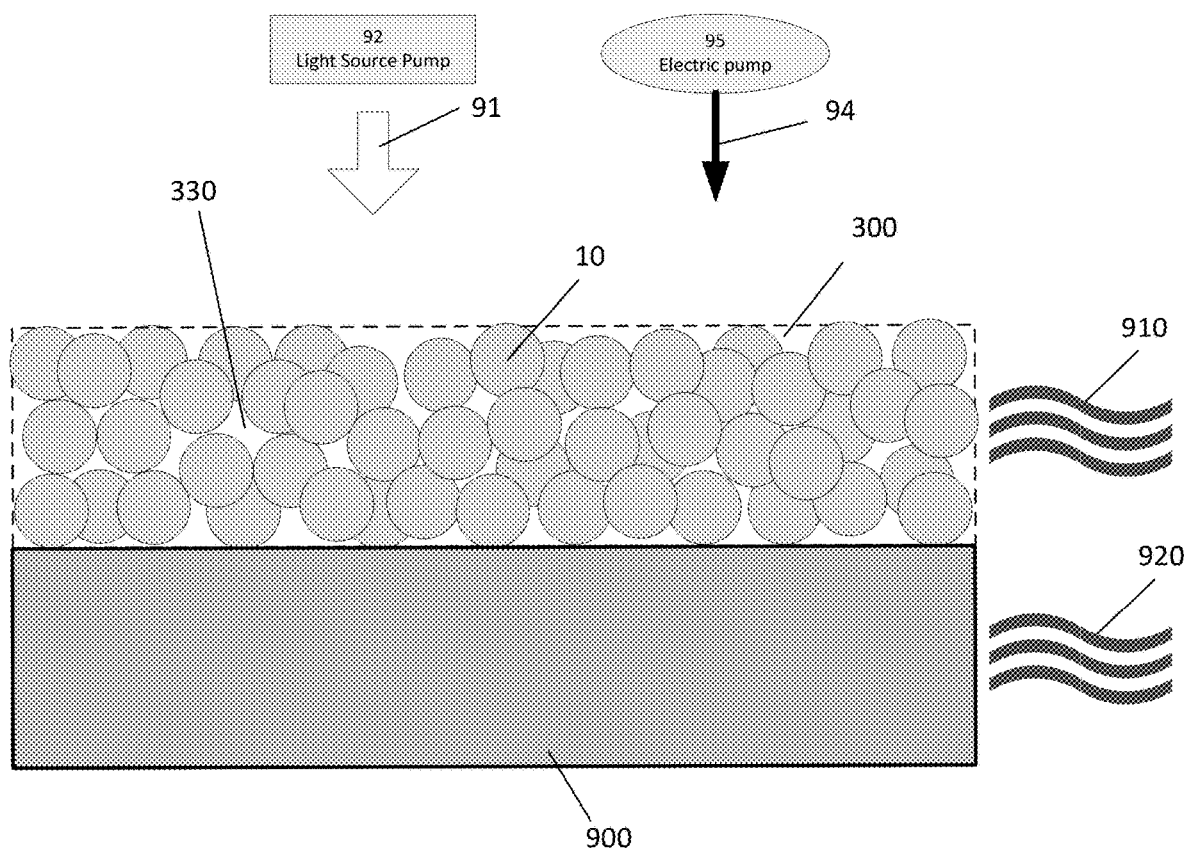
FIG. 9 is an illustration of film of ZnO coupled nanoparticles utilized as a near field power source for an amplified spontaneous emission (ASE) material.

FIG. 9 is an illustration of film 300 of ZnO coupled nanoparticles 10 utilized as a near field power source for an amplified spontaneous emission (ASE) material, arranged in accordance with at least some embodiments presented herein. Those components in FIG. 9 that are labeled identically to components of FIGS. 1-8 will not be described again for the purposes of clarity. Film 300 of ZnO coupled nanoparticles 10 may be formed on a material 900. Material 900 may be an amplified spontaneous emission (ASE) material. Material 900 may include quantum dots. Constructive interference of light due to multiple scattering may be induced in film 300 when film 300 is exposed to a power source such as light source pump 92 or electric pump 95. Film 300 may produce lasing and emit light 910. Light source 92 may be in a vertical direction relative to film 300 and emoted light 910 may be in a horizontal direction relative to film 300. Constructive interference of light due to multiple scattering in film 300 may act as a near field power source to ASE material 900. ASE material 900 may optically amplify energy supplied by film 300 acting as a near field power source and produce lasing and emit light 920. Emitted light 920 may be in a horizontal direction relative to ASE material 900 or in a vertical direction relative to ASE material 900, either by scattering form the film 300 of ZnO coupled nanoparticles 10 or by a patterned grating structure. ASE material 900 may be of a thickness less than a wavelength (λ) of light emitted from ASE material 900 upon lasing.

Among other possible benefits, a system in accordance with the present disclosure may produce films that may be used for integrated photonic applications including fiber-optic communication, biomedical applications, and photonic computing. The disclosed films may be utilized in photonic integrated circuits used in fiber-optic communications systems and quantum computing. The disclosed films may be utilized in lasing devices, for communication devices, and for sensing or detection devices. The disclosed film may be utilized in devices for cleaning with ultraviolet light. The disclosed system may provide low cost, high-efficiency light amplification processes. The disclosed system may provide a laser that is not based on a cavity. The disclosed system may provide lasing in arbitrarily thick samples and may permit fabrication of lasers on any underlying substrate. The disclosed system may provide a laser with broad modes and a low photon lifetime. The disclosed system may provide a laser with a low threshold and a high gain, such as for example, a gain of micro joules per $cm^2$ compared to milli joules per $cm^2$, a gain of two orders of magnitude higher than previous lasers. The disclosed film may display improved lasing properties in films significantly thinner than films previously prepared. Previous films have been prepared by amplified spontaneous emission (ASE) in thin films of nanometer-sized quantum confined nanostructures and prepared by random lasing in larger, micron-sized particles. In ASE, the resulting emission spectrum may be derived from the gain profile of the medium while in random lasing; constructive light interference via multiple scattering may lead to distinct modes in the lasing spectrum. In ASE band engineering strategies may be employed to weaken many-body interactions and reduce losses via non-radiative Auger recombination and reabsorption. In random lasing systems, materials may be chosen that balance scattering losses and gain, by combining strongly scattering nanostructures with a gain medium (such as a laser dye), or by using bifunctional materials that scatter and deliver optical gain simultaneously. Some approaches tune the particle size to optimize resonant scattering at the band-edge emission wavelength for crystalline ZnO spherical particles due to their high refractive index of n=2.3 in ultraviolet light and strong photoluminescence. In these approaches, predictions of an optimal size of ~260 nm radius for crystalline ZnO spherical particles have been achieved, but losses remain high with lasing threshold in the few $mJ/cm^2$ range. The disclosed film is significantly thinner than previously prepared films of ZnO and includes ZnO nanoparticles with a radius of ~35 nm. The disclosed film also exhibits a much lower lasing threshold of <75 $\mu J/cm^2$ than previously prepared films of ZnO.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for fabricating a laser to amplify light, the method comprising:
   depositing nanoparticles on a substrate, wherein the length, width, and height of the nanoparticles are less than 100 nm;
   distributing the nanoparticles on the substrate to produce a film, wherein the nanoparticles in the film are coupled nanoparticles, the coupled nanoparticles are in disordered contact with each other within the film, and the distributing is performed such that constructive interference of the light occurs by multiple scattering at the boundaries of the coupled nanoparticles within the film; and
   exposing the film to a power source.

2. The method of claim 1, wherein the nanoparticles include one of a nitride of Group II-VI semiconductors, an oxide of Group II-VI semiconductors, a nitride of Group ill-V semiconductors, or an oxide of Group III-V semiconductors.

3. The method of claim 1, wherein the nanoparticles include one of zinc oxide or gallium arsenide.

4. The method of claim 1, wherein the distributing of the nanoparticles on the substrate includes one of spin coating, nanoimprint lithography, dip coating, inkjet printing, and matrix-assisted pulse laser evaporation.

5. The method of claim 1, wherein the nanoparticles are zinc oxide nanospheres with a radius of between 35 nm to 50 nm.

6. The method of claim 5, wherein the distributing of the nanospheres on the substrate further comprises distributing the nanospheres on the substrate so that the film is 3 to 4 zinc oxide nanospheres thick.

7. The method of claim 1, wherein the power source is a light source pump or an electric pump.

8. The method of claim 1, further comprising interspersing a dielectric material between the nanoparticles through atomic layer deposition.

9. The method of claim 1, wherein the distributing the nanoparticles on the substrate further comprises:
spin coating the nanoparticles on the substrate at 8,000 rpm to 12,000 rpm; and
heating the substrate to a temperature between 250° C. to 350° C.; and
wherein the nanoparticles are zinc oxide nanospheres with a radius of between 35 nm to 45 nm and the film is 3 to 4 zinc oxide nanospheres thick.

10. A laser comprising:
a power source effective to produce light;
a substrate in communication with the power source, where the substrate includes a film, the film includes nanoparticles, wherein the length, width, and height of the nanoparticles are below 100 nm, the nanoparticles in the film are coupled nanoparticles, wherein the coupled nanoparticles are in disordered contact with each other within the film, and a distribution of the coupled nanoparticles on the substrate is effective to produce constructive interference of the light by multiple scattering at the boundaries of the coupled nanoparticles within the film.

11. The laser of claim 10, wherein the nanoparticles include one of a nitride of Group II-VI semiconductors, an oxide of Group II-VI semiconductors, a nitride of Group III-V semiconductors, or an oxide of Group III-V semiconductors.

12. The laser of claim 10, wherein the nanoparticles include one of zinc oxide or gallium arsenide.

13. The laser of claim 10, wherein the nanoparticles are zinc oxide nanospheres with a radius of between 35 nm to 50 nm.

14. The laser of claim 13, wherein the film is 3 to 4 zinc oxide nanospheres thick.

15. The laser of claim 10, wherein the substrate includes an amplified spontaneous emission (ASE) material.

16. The laser of claim 10, wherein the coupled nanoparticles are interspersed with a dielectric material.

17. A sensing device comprising:
a substrate;
a film on the substrate, wherein the film includes nanoparticles, the length, width, and height of the nanoparticles are below 100 nm, the nanoparticles in the film are coupled nanoparticles the coupled nanoparticles are in disordered contact with each other within the film, and a distribution of the coupled nanoparticles on the substrate is effective to produce constructive interference of a first light by multiple scattering at boundaries of the coupled nanoparticles within the film;
a sensing element in optical communication with the film, wherein the film is effective to receive the first light and emit second light and a quantity of lumens of the second light is greater than a quantity of lumens of the first light, the sensing element is effective to detect the second light and generate a response.

18. The sensing device of claim 17, wherein the nanoparticles include one of a nitride of Group II-VI semiconductors, an oxide of Group II-VI semiconductors, a nitride of Group IIIV semiconductors, or an oxide of Group III-V semiconductors.

19. The sensing device of claim 17, wherein the nanoparticles include zinc oxide or gallium arsenide.

20. The sensing device of claim 17, wherein the nanoparticles are zinc oxide nanospheres with a radius of between 35 nm to 50 nm.

* * * * *